(12) United States Patent
Coenen et al.

(10) Patent No.: US 10,531,992 B2
(45) Date of Patent: Jan. 14, 2020

(54) ABSORBENT ARTICLE HAVING A ONE-PIECE CHASSIS AND INTEGRAL SIDE PORTIONS

(71) Applicant: Kimberly-Clark Worldwide, Inc., Neenah, WI (US)

(72) Inventors: Joseph Daniel Coenen, Kaukauna, WI (US); Andrew Edward Neubauer, Neenah, WI (US); Michael Donald Sperl, Waupaca, WI (US); Frederique Vignali, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 351 days.

(21) Appl. No.: 14/911,641

(22) PCT Filed: Dec. 19, 2014

(86) PCT No.: PCT/US2014/071654
§ 371 (c)(1),
(2) Date: Feb. 11, 2016

(87) PCT Pub. No.: WO2016/099566
PCT Pub. Date: Jun. 23, 2016

(65) Prior Publication Data
US 2017/0258644 A1    Sep. 14, 2017

(51) Int. Cl.
*A61F 13/15* (2006.01)
*A61F 13/49* (2006.01)
*A61F 13/496* (2006.01)

(52) U.S. Cl.
CPC .... *A61F 13/4906* (2013.01); *A61F 13/15699* (2013.01); *A61F 13/496* (2013.01); *A61F 13/49012* (2013.01); *A61F 13/49015* (2013.01); *A61F 2013/49053* (2013.01)

(58) Field of Classification Search
CPC ............ A61F 13/4906; A61F 13/15699; A61F 13/49012; A61F 13/49015; A61F 2013/49053
USPC .............. 604/385.24, 385.27, 385.29, 385.3, 604/385.22
See application file for complete search history.

(56) References Cited

U.S. PATENT DOCUMENTS

| | | | |
|---|---|---|---|
| 4,427,408 A | 1/1984 | Karami et al. | |
| 4,704,116 A * | 11/1987 | Enloe | A61F 13/49009 604/358 |
| 5,246,433 A * | 9/1993 | Hasse | A61F 13/49009 604/358 |
| 5,545,158 A * | 8/1996 | Jessup | A61F 13/49011 604/373 |
| 6,514,233 B1 | 2/2003 | Glaug | |
| 6,793,650 B2 | 9/2004 | Weber | |
| 7,056,313 B2 | 6/2006 | Franke et al. | |
| 7,662,138 B2 | 2/2010 | Hermansson et al. | |
| 7,799,007 B2 | 9/2010 | Hermansson et al. | |
| 8,211,080 B2 | 7/2012 | Ruman et al. | |
| 8,475,424 B2 | 7/2013 | Fujimoto et al. | |

(Continued)

*Primary Examiner* — Jacqueline F Stephens
(74) *Attorney, Agent, or Firm* — Kimberly-Clark Worldwide, Inc.

(57) ABSTRACT

An absorbent article which has a one-piece chassis and integral side portions. The one-piece chassis can be a bi-laminate material and can have a liquid permeable layer and a liquid impermeable layer bonded together. The side portions can be integrally formed from the one-piece chassis.

18 Claims, 5 Drawing Sheets

(56) References Cited

U.S. PATENT DOCUMENTS

| | | |
|---|---|---|
| 2006/0241560 A1 | 10/2006 | Chang et al. |
| 2008/0082073 A1 | 4/2008 | Driskell et al. |
| 2008/0287904 A1 | 11/2008 | Drevik et al. |
| 2010/0168706 A1 | 7/2010 | Vasic |
| 2010/0241097 A1 | 9/2010 | Nigam et al. |
| 2010/0286647 A1 | 11/2010 | Back et al. |
| 2010/0305536 A1 | 12/2010 | Fernkvist et al. |
| 2012/0078212 A1 | 3/2012 | Kobayashi et al. |
| 2012/0152436 A1 | 6/2012 | Schneider |
| 2012/0277712 A1 | 11/2012 | Schmitz |

* cited by examiner

ABSORBENT ARTICLE HAVING A ONE-PIECE CHASSIS AND INTEGRAL SIDE PORTIONS

BACKGROUND OF THE DISCLOSURE

A primary function of personal care absorbent articles is to absorb and retain body exudates, such as urine and fecal material, with additional desired attributes including low leakage of the body exudates from the absorbent article, a conforming fit of the absorbent article to the wearer's body, and a dry feel to the wearer of the absorbent article.

As the usage of absorbent articles has expanded, their complexity has increased due to the incorporation of additional features serving to enhance their performance and appearance. The increase in complexity of the absorbent article has resulted in absorbent articles containing many pieces which are required to be attached to each other in order to form a complete, useable and wearable absorbent article. The resultant absorbent article, therefore, may have seams, joints and connection points which can provide an unfinished appearance to the consumer. The seams, joints and connection points can also increase the number of locations where the materials of the absorbent article may rub against the wearer's skin resulting in discomfort to the wearer. Two materials brought together at a seam, joint and/or connection point may not be fully attached to each other and/or one or both materials may not have a completely smooth edge. Such materials can rub against the skin of the wearer resulting in chafing, red marks, damaged skin, and overall soreness in the area of the rubbing.

The costs of the materials and the costs of the manufacturing processes have also increased in conjunction with the increases in complexity. As a result, the prices at which these articles are sold have risen to levels that many potential consumers cannot afford to pay. Attempts have been made in the past to provide an absorbent article at a lower cost for both the consumer and the manufacturer. Such attempts, however, may result in an absorbent article which does not provide the desired attributes. For example, an attempt to provide an absorbent article at a lower cost may result in an absorbent article having materials which may not minimize leakage of body exudates from the absorbent article. As another example, an attempt to provide an absorbent article at a lower cost may result in an absorbent article which may not adequately conform to a wearer's body.

A need exists for a simplified absorbent article. A need exists for an absorbent article which can provide the desired attributes of leakage protection, conformance to body, and a dry feel to the wearer without causing discomfort to the wearer due to loose materials, cut edges of the materials, and/or rubbing of the materials against the skin of the wearer. A need exists for an absorbent article which can provide the desired attributes of leakage protection, conformance to the body, and a dry feel to the wearer at a lower cost to the consumer and manufacturer.

SUMMARY OF THE DISCLOSURE

In various embodiments, an absorbent article can have a one-piece chassis comprising a chassis material and defining a front waist region, a back waist region, and a crotch region interconnecting the front waist region and the back waist region; an opposing pair of front side portions integral with the chassis in the front waist region; an opposing pair of back side portions integral with the chassis in the back waist region; and at least two of the front side portions or the back side portions comprising at least a first layer of the chassis material and a second layer of the chassis material and a fold connecting the first layer of chassis material and the second layer of chassis material. In various embodiments, the chassis material is a single layer of material. In various embodiments, the chassis material is a laminate of two layers of material. In various embodiments, a first layer of material is a liquid permeable material and a second layer of material is a liquid impermeable material. In various embodiments, each of the side portions comprises a wearer facing surface and a garment facing surface and a portion of the liquid permeable material is located on at least a portion of the wearer facing surface of each of the side portions. In various embodiments, the absorbent article further has an absorbent assembly bonded to the chassis. In various embodiments, the chassis material is at least stretchable in a lateral direction.

In various embodiments, an absorbent article can have a one-piece chassis comprising a chassis material and defining a front waist region, a back waist region, and a crotch region interconnecting the front waist region and the back waist region; an opposing pair of front side portions integral with the chassis in the front waist region; an opposing pair of back side portions integral with the chassis in the back waist region; at least two of the front side portions or the back side portions comprising at least a first layer of the chassis material and a second layer of the chassis material and a fold connecting the first layer of the chassis material and the second layer of the chassis material; and an absorbent assembly bonded to the chassis material. In various embodiments, the chassis material is a single layer of material. In various embodiments, the chassis material is a laminate of two layers of material. In various embodiments, a first layer of material is a liquid permeable material and a second layer of material is a liquid impermeable material. In various embodiments, each of the side portions comprises a wearer facing surface and a garment facing surface and a portion of the liquid permeable material is located on at least a portion of the wearer facing surface of each of the side portions. In various embodiments, the chassis material is at least stretchable in a lateral direction.

In various embodiments, a method of manufacturing an absorbent article can have the steps of providing a chassis material; cutting the chassis material to create a flap in the chassis material; folding the flap over a portion of the chassis material; and bonding an absorbent assembly to the chassis material. In various embodiments, the step of cutting the chassis material further comprises the step of incorporating a transverse direction cut and a longitudinal direction cut into the chassis material. In various embodiments, the chassis material is a single layer of material. In various embodiments, the chassis material is a laminate of two layers of material. In various embodiments, the method further has the step of bonding the flap to the chassis material. In various embodiments, the chassis material is at least stretchable in a lateral direction.

Figure 1:
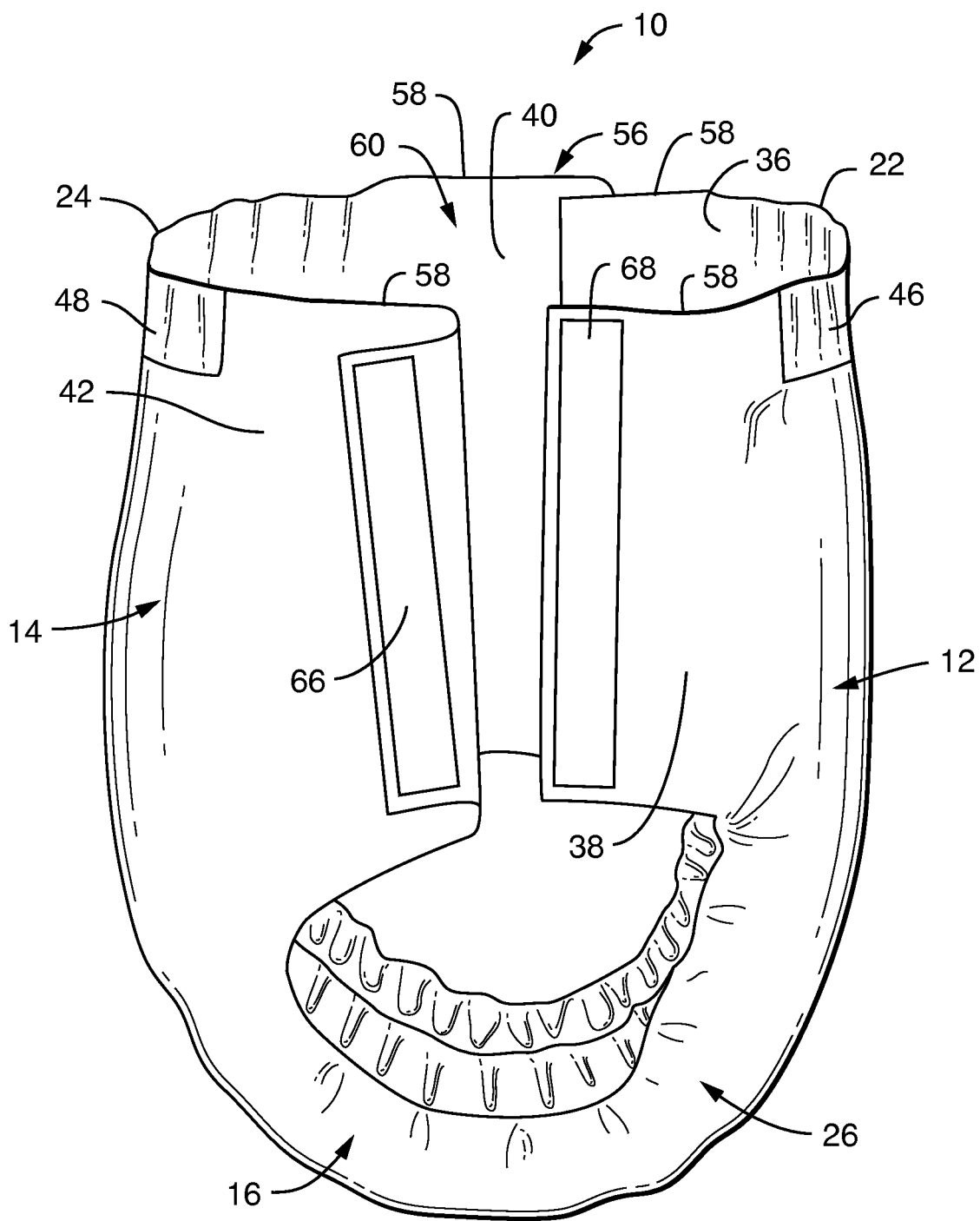
FIG. 1 is a side view of an embodiment of an absorbent article.

Repeat use of reference characters in the present specification and drawings is intended to represent the same or analogous features or elements of the disclosure.

DETAILED DESCRIPTION OF THE DISCLOSURE

In various embodiments, the present disclosure is generally directed towards an absorbent article which can have a one-piece chassis and integral side portions. In various embodiments, the material of the one-piece chassis can be utilized to form the integral side portions in accordance with a manufacturing process of the present disclosure. Without being bound by theory, it is believed that the present disclosure can increase manufacturing potential by increasing material utilization and decreasing waste during the manufacturing process. It is also believed that a one-piece chassis can provide an integral appearance to the consumer and the decrease in the number of seams, joints and connection points can decrease the incidence of rubbing to the wearer of the absorbent article.

Definitions

The term "absorbent article" refers herein to an article which may be placed against or in proximity to the body (i.e., contiguous with the body) of the wearer to absorb and contain various liquids and solid wastes discharged from the body. Such absorbent articles, as described herein, are intended to be discarded after a limited period of use instead of being laundered or otherwise restored for reuse. It is to be understood that the present disclosure is applicable to various disposable absorbent articles, including, but not limited to, diapers, training pants, youth pants, diaper pants, swim pants, feminine hygiene products, incontinence products, medical garments, other personal care or health care garments, and the like without departing from the scope of the present disclosure.

The term "acquisition layer" refers herein to a layer capable of accepting and temporarily holding liquid body waste to decelerate and diffuse a surge or gush of liquid body waste and to subsequently release the liquid body waste therefrom into another layer or layers of the absorbent article.

The term "bonded" refers herein to the joining, adhering, connecting, attaching, or the like, of two elements. Two elements will be considered bonded together when they are joined, adhered, connected, attached, or the like, directly to one another or indirectly to one another, such as when each is directly bonded to intermediate elements.

The term "carded web" refers herein to a web containing natural or synthetic staple length fibers typically having fiber lengths less than about 100 mm. Bales of staple fibers can undergo an opening process to separate the fibers which are then sent to a carding process which separates and combs the fibers to align them in the machine direction after which the fibers are deposited onto a moving wire for further processing. Such webs are usually subjected to some type of bonding process such as thermal bonding using heat and/or pressure. In addition to or in lieu thereof, the fibers may be subject to adhesive processes to bind the fibers together such as by the use of powder adhesives. The carded web may be subjected to fluid entangling, such as hydroentangling, to further intertwine the fibers and thereby improve the integrity of the carded web. Carded webs, due to the fiber alignment in the machine direction, once bonded, will typically have more machine direction strength than cross machine direction strength.

The term "film" refers herein to a thermoplastic film made using an extrusion and/or forming process, such as a cast film or blown film extrusion process. The term includes apertured films, slit films, and other porous films which constitute liquid transfer films, as well as films which do not transfer fluids, such as, but not limited to, barrier films, filled films, breathable films, and oriented films.

The term "fluid entangling" and "fluid entangled" refers herein to a formation process for further increasing the degree of fiber entanglement within a given fibrous nonwoven web or between fibrous nonwoven webs and other materials so as to make the separation of the individual fibers and/or the layers more difficult as a result of the entanglement. Generally this is accomplished by supporting the fibrous nonwoven web on some type of forming or carrier surface which has at least some degree of permeability to the impinging pressurized fluid. A pressurized fluid stream (usually multiple streams) can then be directed against the surface of the nonwoven web which is opposite the supported surface of the web. The pressurized fluid contacts the fibers and forces portions of the fibers in the direction of the fluid flow thus displacing all or a portion of a plurality of the fibers towards the supported surface of the web. The result is a further entanglement of the fibers in what can be termed the Z-direction of the web (its thickness) relative to its more planar dimension, its X-Y plane. When two or more separate webs or other layers are placed adjacent one another on the forming/carrier surface and subjected to the pressurized fluid, the generally desired result is that some of the fibers of at least one of the webs are forced into the adjacent web or layer thereby causing fiber entanglement between the interfaces of the two surfaces so as to result in the bonding or joining of the webs/layers together due to the increased entanglement of the fibers. The degree of bonding or entanglement will depend on a number of factors including, but not limited to, the types of fibers being used, the fiber lengths, the degree of pre-bonding or entanglement of the web or webs prior to subjection to the fluid entangling process, the type of fluid being used (liquids, such as water, steam or gases, such as air), the pressure of the fluid, the number of fluid streams, the speed of the process, the dwell time of the fluid and the porosity of the web or webs/other layers and the forming/carrier surface. One of the most common fluid entangling processes is referred to as hydroentangling which is a well-known process to those of ordinary skill in the art of nonwoven webs. Examples of fluid entangling process can be found in U.S. Pat. No. 4,939,016 to Radwanski et al., U.S. Pat. No. 3,485,706 to Evans, and U.S. Pat. Nos. 4,970,104 and 4,959,531 to Radwanski, each of which is incorporated herein in its entirety by reference thereto for all purposes.

The term "g/cc" refers herein to grams per cubic centimeter.

The term "gsm" refers herein to grams per square meter.

The term "hydrophilic" refers herein to fibers or the surfaces of fibers which are wetted by aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by Cahn SFA-222 Surface Force Analyzer System, or a substantially equivalent system. When measured with this system, fibers having contact angles less than 90 are designated "wettable" or hydrophilic, and fibers having contact angles greater than 90 are designated "nonwettable" or hydrophobic.

The term "liquid impermeable" refers herein to a layer or multi-layer laminate in which liquid body exudates, such as urine, will not pass through the layer or laminate, under ordinary use conditions, in a direction generally perpendicular to the plane of the layer or laminate at the point of liquid contact.

The term "liquid permeable" refers herein to any material that is not liquid impermeable.

The term "meltblown" refers herein to fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter, which can be a microfiber diameter. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin et al., which is incorporated herein by reference. Meltblown fibers are microfibers which may be continuous or discontinuous, are generally smaller than about 0.6 denier, and may be tacky and self-bonding when deposited onto a collecting surface.

The term "nonwoven" refers herein to materials and webs of material which are formed without the aid of a textile weaving or knitting process. The materials and webs of materials can have a structure of individual fibers, filaments, or threads (collectively referred to as "fibers") which can be interlaid, but not in an identifiable manner as in a knitted fabric. Nonwoven materials or webs can be formed from many processes such as, but not limited to, meltblowing processes, spunbonding processes, carded web processes, etc.

The term "pliable" refers herein to materials which are compliant and which will readily conform to the general shape and contours of the wearer's body.

The term "spunbond" refers herein to small diameter fibers which are formed by extruding molten thermoplastic material as filaments from a plurality of fine capillaries of a spinnerette having a circular or other configuration, with the diameter of the extruded filaments then being rapidly reduced by a conventional process such as, for example, eductive drawing, and processes that are described in U.S. Pat. No. 4,340,563 to Appel et al., U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Peterson, and U.S. Pat. No. 3,542,615 to Dobo et al., each of which is incorporated herein in its entirety by reference. Spunbond fibers are generally continuous and often have average deniers larger than about 0.3, and in an embodiment, between about 0.6, 5 and 10 and about 15, 20 and 40. Spunbond fibers are generally not tacky when they are deposited on a collecting surface.

The term "superabsorbent" refers herein to a water-swellable, water-insoluble organic or inorganic material capable, under the most favorable conditions, of absorbing at least about 15 times its weight and, in an embodiment, at least about 30 times its weight, in an aqueous solution containing 0.9 weight percent sodium chloride. The superabsorbent materials can be natural, synthetic and modified natural polymers and materials. In addition, the superabsorbent materials can be inorganic materials, such as silica gels, or organic compounds, such as cross-linked polymers.

The term "thermoplastic" refers herein to a material which softens and which can be shaped when exposed to heat and which substantially returns to a non-softened condition when cooled.

Absorbent Article:

Referring to FIG. 1, a disposable absorbent article 10 of the present disclosure is exemplified in the form of a pant, such as, for example, a training pant in a partially assembled configuration. It is to be understood that the present disclosure is suitable for use with various other personal care absorbent articles, such as, for example, diapers, youth pants, diaper pants, swim pants, incontinence products, and feminine hygiene products, without departing from the scope of the present disclosure.

The absorbent article 10 includes a front waist region 12, a back waist region 14, and a crotch region 16 interconnecting the front waist region 12 and the back waist region 14. The absorbent article 10 can have a pair of opposing longitudinal direction side edges, 18 and 20 (shown in FIGS. 2 and 3). The absorbent article 10 can have a pair of opposing waist edges, respectively designated front waist edge 22 and back waist edge 24. The front waist region 12 can be contiguous with the front waist edge 22 and the back waist region 14 can be contiguous with the back waist edge 24. The front waist region 12 can include the portion of the absorbent article 10 that, when worn, is positioned at least in part on the front of the wearer while the back waist region 14 can include the portion of the absorbent article 10 that, when worn, is positioned at least in part on the back of the wearer. The crotch region 16 of the absorbent article 10 can include the portion of the absorbent article 10 that, when worn, is positioned between the legs of the wearer and can partially cover the lower torso of the wearer.

The absorbent article 10 can include a chassis 26 and an absorbent assembly 28. The absorbent article 10 can have a longitudinal axis 30 and a lateral axis 32. The absorbent assembly 28 can extend longitudinally from the front waist region 12 through the crotch region 16 to the back waist region 14. While the absorbent assembly 28 is shown and described herein as extending from the crotch region 16 into both the front and back waist regions, 12 and 14, it is contemplated that the absorbent assembly 28 may extend from the crotch region 16 into primarily the front waist region 12, or into primarily the back waist region 14. In various embodiments, the absorbent assembly 28 may extend any suitable length along the crotch region 16 and/or into the front waist region 12 and/or into the back waist region 14. In various embodiments, the chassis 26 can define a length and a width which can coincide with the length and width of the absorbent article 10. The longitudinal direction and the lateral direction of the absorbent article 10, and of the materials which form the absorbent article 10, can provide the X-Y planes, respectively, of the absorbent article 10 and of the materials which form the absorbent article 10.

In various embodiments, the chassis 26 and the absorbent assembly 28 can be formed separately from one another. In various embodiments, the chassis 26 and the absorbent assembly 28 can be integrally formed with one another. In various embodiments, the absorbent assembly 28 can be disposable and the chassis 26 can be non-disposable.

Figure 2:
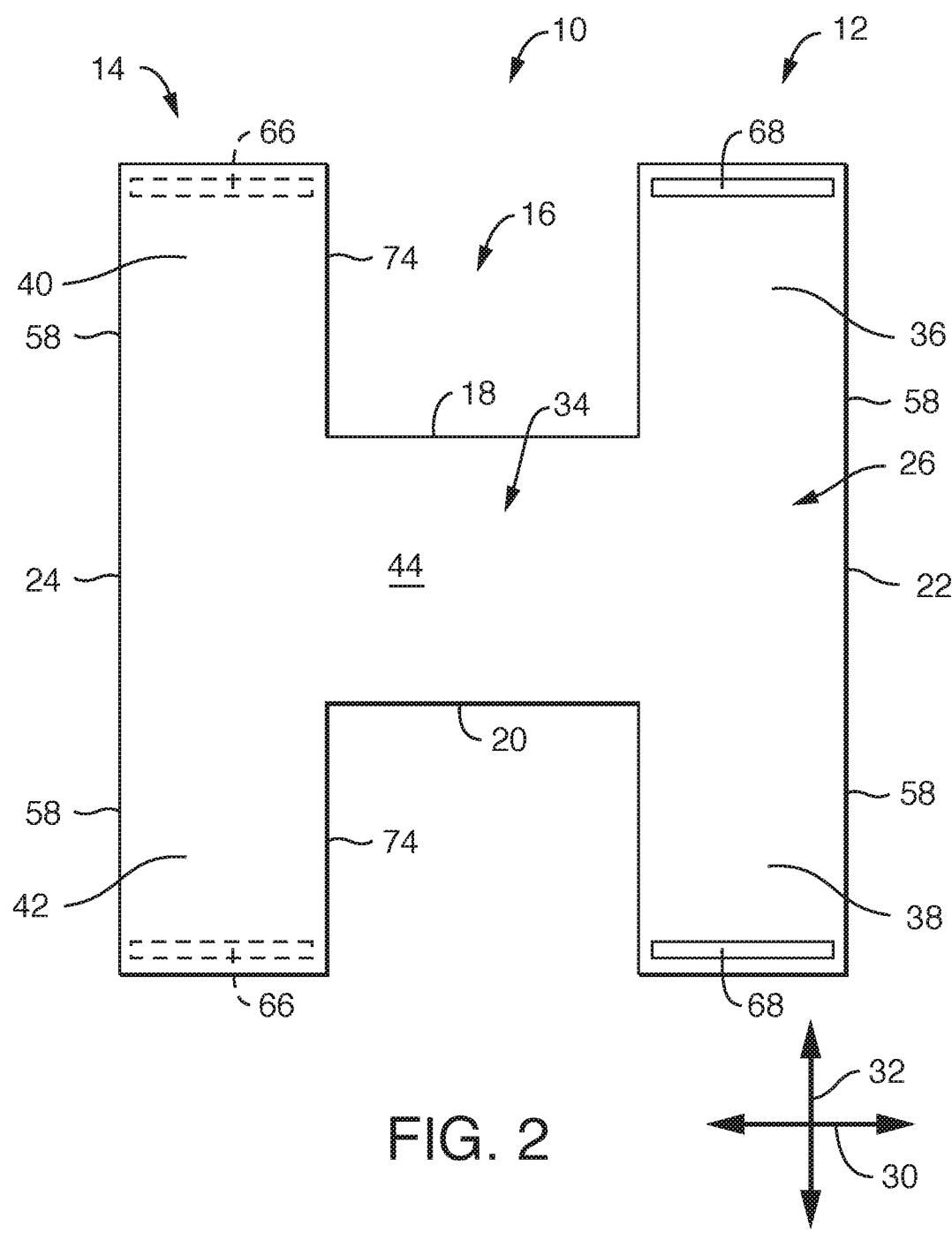
FIG. 2 is a bottom plan view of the absorbent article of FIG. 1 in an unfastened, unfolded and laid flat condition and showing the surface of the absorbent article that faces away from the wearer.
Figure 3:
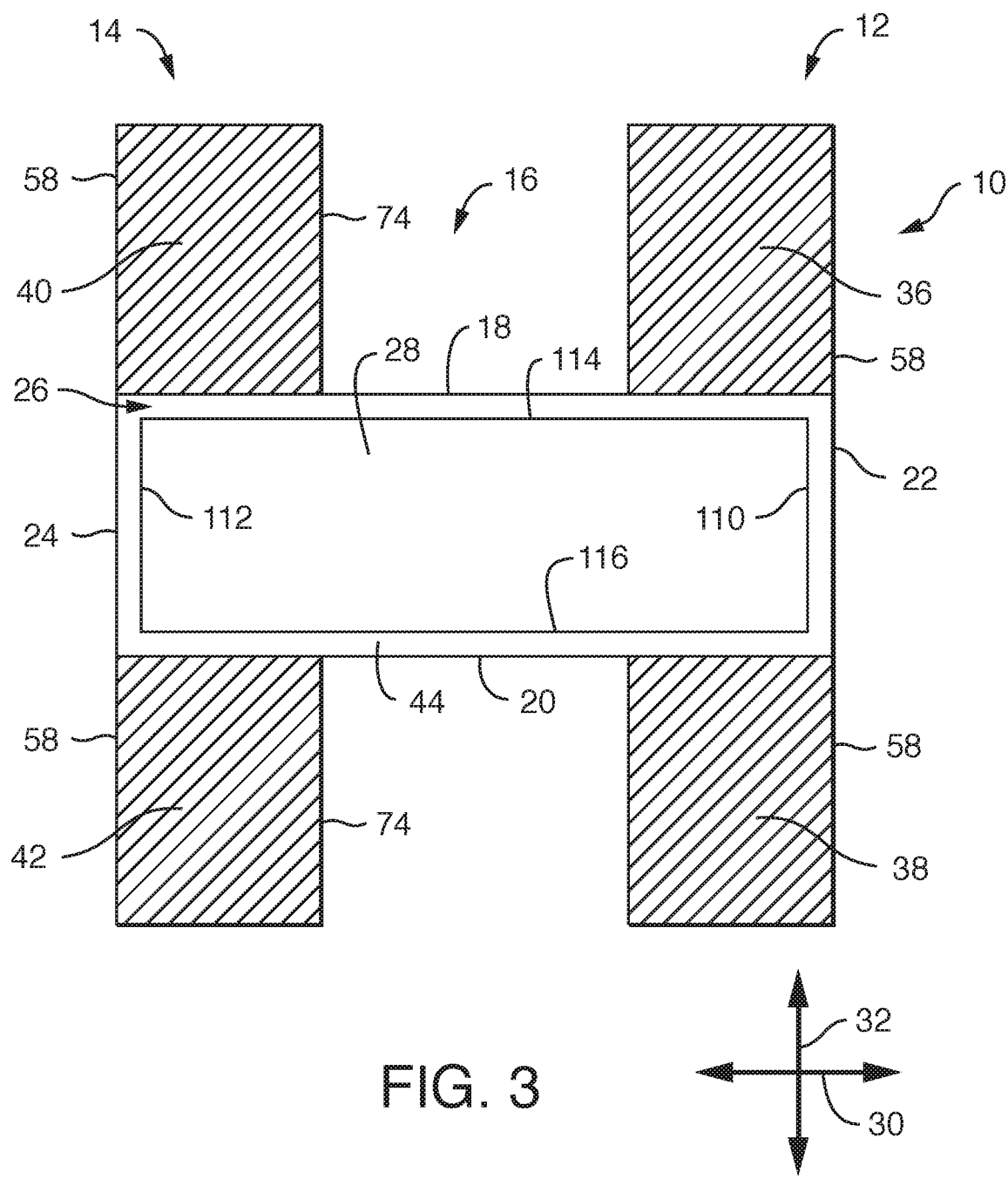
FIG. 3 is a top plan view of the absorbent article of FIG. 1 in an unfastened, unfolded and laid flat condition and showing the surface of the absorbent article that faces the wearer.

As illustrated in FIGS. 2 and 3, the chassis 26 can have a longitudinally extending central portion 34, a pair of laterally opposite front side portions, 36 and 38, extending outward from the central portion 34 at the front waist region 12 (thereby forming transversely outer portions of the front waist region 12) and a pair of laterally opposite back side portions, 40 and 42, extending outward from the central portion 34 at the back waist region 14 (thereby forming transversely outer portions of the back waist region 14). In various embodiments, the central portion 34 can extend from the front waist region 12 through the crotch region 16 to the back waist region 14 of the absorbent article 10.

The front side portions, 36 and 38, and the back side portions, 40 and 42, of the absorbent article 10 are formed integrally with the chassis 26 of the absorbent article 10. The material 44 utilized for the chassis 26 can be utilized to form the side portions, 36, 38, 40 and 42. As will be described herein, during a manufacturing process to assemble the absorbent article 10, the chassis 26 material 44 can be subjected to a laterally opposing pair of coordinated and connecting cuts. Each pair of cuts can have a machine-direction cut 50 and a cross-machine-direction cut 52 (illustrated in FIG. 4). The coordinated and connecting cuts, 50 and 52, can create a flap 54 in the chassis 26 material 44 which can be folded back over a portion of the chassis 26 material 44 in the formation of the side portions, 36, 38, 40 and 42.

To assemble the absorbent article illustrated in FIG. 1, the front waist region 12 can be bonded to the back waist region 14 via the formation of an engagement seam 56 between a front side portion, such as front side portion 36, and a back side portion, such as back side portion 40. Each of the front side portions, 36 and 38, and each of the back side portions, 40 and 42, can have a waist end edge 58 disposed toward a longitudinal end of the absorbent article 10. The waist edges, 22 and 24, and the waist end edges 58 of each of the side portions, 36, 38, 40 and 42, are configured to encircle the waist of the wearer and together at least partially define the central waist opening 60. When worn, the absorbent article 10 has a pair of leg openings which can be defined at least in part by the longitudinal side edges, 18 and 20, and the side portions, 36, 38, 40 and 42 of the absorbent article 10.

Additional details regarding each of these elements of the absorbent article 10 described herein can be found below and with reference to FIGS. 1-5.

Chassis:

The chassis 26 can be liquid permeable or liquid impermeable. The chassis 26 can be breathable and/or liquid impermeable. The chassis 26 can be elastic, stretchable or non-stretchable. The chassis 26 may be constructed of a single layer, multiple layers, laminates, spunbond fabrics, films, meltblown fabrics, elastic netting, microporous webs, bonded-carded webs or foams provided by elastomeric or polymeric materials. In an embodiment, the chassis 26 can be a single layer of a liquid impermeable material. In an embodiment, the chassis 26 can be a single layer of a liquid permeable material. In an embodiment, the chassis 26 can be suitably stretchable, and more suitably elastic, in at least the lateral 32 or circumferential direction of the absorbent article 10. In an embodiment, the chassis 26 can be stretchable, and more suitably elastic, in both the lateral 32 and the longitudinal 30 directions. In an embodiment, the chassis 26 can be a multi-layered laminate in which each of the layers is liquid permeable. In an embodiment, the chassis 26 can be a multi-layered laminate in which at least one of the layers is liquid impermeable. In an embodiment, the chassis 26 may be a laminate of two layer construction, including an outer layer constructed of a liquid permeable material and an inner layer constructed of liquid impermeable material bonded together by a laminate adhesive. Suitable laminate adhesives can be applied continuously or intermittently as beads, a spray, parallel swirls, or the like. Suitable adhesives can be obtained from Bostik Inc. of Wauwatosa, Wis., U.S.A. It is to be understood that the inner layer can be bonded to the outer layer utilizing ultrasonic bonds, thermal bonds, pressure bonds, or the like. In an embodiment, the chassis 26 can be engageable such as, for example, the chassis 26 can have an adhesive material, a cohesive material, a mechanical engagement, and the like, present on a surface of the chassis 26 material 44. In an embodiment, the chassis 26 material 44 can be self-engageable such as, for example, a surface of the chassis 26 material 44 can be brought into contact with another surface of the chassis 26 material 44 and each surface can have a cohesive material thereupon and each cohesive material can exhibit an affinity for the other cohesive material thereby bonding the two portions of the chassis 26 material 44 to one another.

The liquid permeable outer layer of the chassis 26 can be any suitable material and may be one that provides a generally cloth-like texture to the wearer. An example of such material can be a 100% polypropylene bonded-carded web with a diamond bond pattern available from Sandler A. G., Germany such as 30 gsm Sawabond 4190® or equivalent. Another example of material suitable for use as an outer layer of a chassis 26 can be a 20 gsm spunbond polypropylene non-woven web. The outer layer may also be constructed of the same materials from which the bodyside liner 28 is constructed as described herein. It is to be understood that it is not necessary for the outer layer of the chassis 26 to be liquid permeable.

The liquid impermeable inner layer of the chassis 26 can be either vapor permeable (i.e., "breathable") or vapor impermeable. The inner layer may be manufactured from a thin plastic film, although other liquid impermeable materials may also be used. The liquid impermeable inner layer (or the liquid impermeable chassis 26 where the chassis 26 is of a single-layer construction) can inhibit liquid body waste from leaking out of the absorbent article 10 and wetting articles, such as bed sheets and clothing, as well as the wearer and caregiver. An example of a material for an inner layer can be a printed 19 gsm XP-8695H or 8790C film or equivalent commercially available from Berry Corporation, Schaumburg, Ill., U.S.A.

Where the chassis 26 is of a single layer construction, it can be embossed and/or matte finished providing a more cloth-like appearance. The chassis 26 can permit vapors to escape from the absorbent article 10 while preventing liquids from passing through. A suitable liquid impermeable, vapor permeable material can be composed of a microporous polymer film or a non-woven material which has been coated or otherwise treated to impart a desired level of liquid impermeability.

Figure 4:
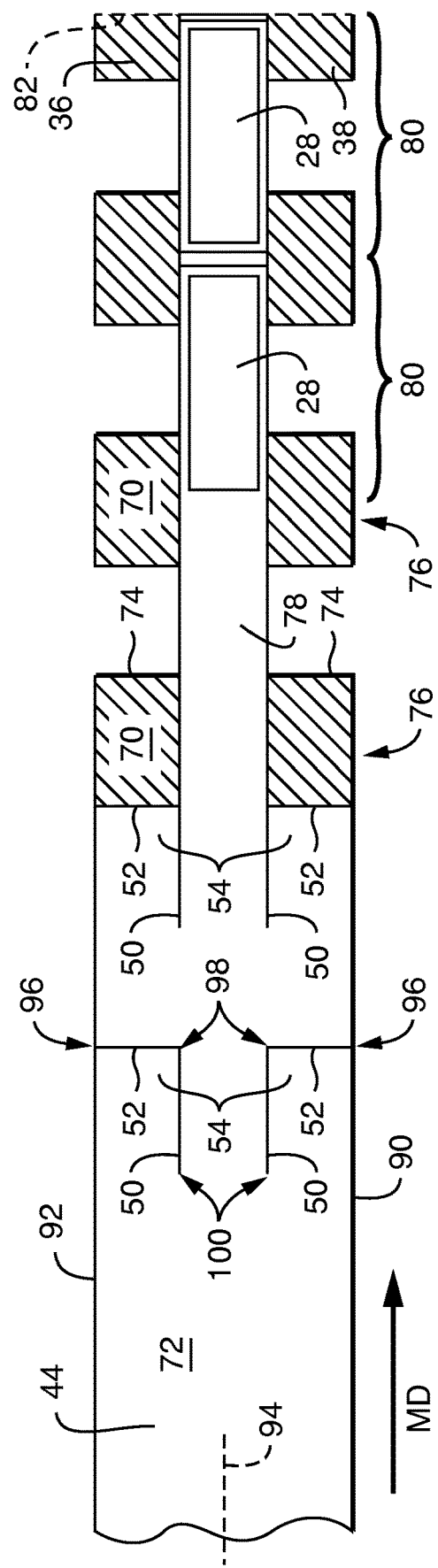
FIG. 4 is a schematic illustration of an absorbent article being assembled in accordance with a non-limiting embodiment of the present disclosure.

FIG. 4 provides an exemplary schematic of a continuous manufacturing process for the manufacture of an absorbent article 10. In the manufacturing process illustrated in FIG. 4, a single material 44 can be utilized to form the chassis 26 in the front waist region 12, the back waist region 14 and the crotch region 16 as well as form the side portions, 36, 38, 40 and 42 of the absorbent article 10. The resultant absorbent article 10 can, therefore, have a one-piece chassis design with integral side portions, 36, 38, 40 and 42.

In the embodiment illustrated in FIG. 4, the material 44 can be of a bi-laminate construction having an outer layer 70 constructed of a liquid permeable material and an inner layer 72 constructed of liquid impermeable material bonded together by a laminate adhesive. It should be understood that a material 44 having a single layer of material, such as, for example, a single layer of a liquid impermeable material can also be utilized.

During the manufacturing process, a continuous material 44 having an opposing pair of longitudinal direction edges, 90 and 92, can be provided. A portion of the material 44 can be subjected to a laterally opposing pair of coordinated and connecting cuts. Each pair of coordinated and connecting cuts can have a machine-direction (MD) cut 50 and a cross-machine-direction cut 52. Each of the cross-machine direction cuts 52 can begin at one of the respective longitudinal direction edges, 90 or 92, of the material 44 and extend inward towards the centerline 94 of the material 44. In various embodiments, the length of each of the cross-machine direction cuts 52 can be less than about ⅓ of the total length between the longitudinal direction side edges, 90 and 92, of the material 44. A cross-machine direction cut 52 can, therefore, have a first terminus 96 located at one of the longitudinal direction side edges, 90 or 92, of the material 44 and a second terminus 98 located inward of the longitudinal direction side edge, 90 or 92. The machine-direction cut 50 can connect with the cross-machine direction cut 52 and can extend a portion of the longitudinal length of the material 44. In various embodiments, the length of each machine-direction cut 50 can be about ½ of the desired overall length of a resultant absorbent article 10. The machine-direction cut 50 can have a first terminus 98, which is the same as the second terminus 98 of the cross-machine direction cut 52, and a second terminus 100 which ends the cut of the material 44.

The coordinated and connecting cuts, 50 and 52, can create a flap 54 in the material 44. In various embodiments, the flap 54 can be a rectangle or square shape in which three side are free from the material 44 and one side remains bound to the material 44. It should be realized that a flap 54 in the shape of a rectangle or square can be provided by machine direction cuts 50 and cross-machine direction cuts 52 which are straight. It should be realized that the machine direction cuts 50 and/or the cross-machine direction cuts 52 can be provided with an arcuate or sinusoidal shape. Such arcuate or sinusoidal shapes can allow for curved edges in the leg openings of the resultant absorbent article 10. The flap 54 can be folded back over a portion of the material 44 and bonded to that portion of the material 44 over which it now covers. Folding of the flap 54 over another portion of the material 44 can increase the rigidity in that particular region of the material 44. The bonding of the flap 54 to the material 44 can occur via any method deemed suitable, such as, but not limited to, adhesive bonding, thermal bonding, embossing, ultrasonic bonding, and/or any other method deemed suitable. In embodiments in which a material 44 is utilized which demonstrates stretchable and/or elastic properties, the bonding of the flap 54 to the material 44 should not occur to such an extent as to overly diminish the stretchable and/or elastic properties of the material 44.

The folding of the flap 54 over a portion of the material 44 can create a fold 74 at the location where the flap 54 was not cut and where the flap 54 remains attached to the material 44. In the embodiment illustrated, as the material 44 is a bi-laminate material 44, the folding of the flap 54 can create a quad-laminate region 76. In the embodiment illustrated, the quad-laminate region 76 can have four layers of material having a structure of liquid permeable material—liquid impermeable material—liquid impermeable material—liquid permeable material. Utilizing a bi-laminate material 44 in the manufacturing process described herein can provide a chassis 26 having a quad-laminate region 76 and a bi-laminate region 78. The bi-laminate region 78 is the portion of the material 44 which was not cut, not folded, and not overlaid by the flap 54. The bi-laminate region 78 can ultimately be located, in a resultant absorbent article 10, in the front waist region 12, back waist region 14, and crotch region 16. In various embodiments in which a single layer of material, such as, for example, a single layer of a liquid impermeable material, is utilized, folding the flap 54 can create a bi-laminate region having a structure of liquid impermeable material—liquid impermeable material. Utilizing a single layer of material 44 in the manufacturing process described herein can provide an absorbent article having a single layer region and a bi-laminate region. In such embodiments, the single layer region can ultimately be located, in a resultant absorbent article 10, in the front waist region 12, back waist region 14, and crotch region 16.

An absorbent assembly 28 can be layered over and bonded to the bi-laminate region 78 of the material 44 (or the single layer region if only a single layer of material is utilized initially). The quad-laminate region 76 of the chassis 26 (or bi-laminate region if only a single layer of material is utilized initially) can ultimately form the side portions, 36, 38, 40 and 42 of the resultant absorbent article 10.

As illustrated in FIG. 4, following the cutting and folding of the flap 54 of the material 44, an absorbent assembly 28 can be positioned over and bonded to the bi-laminate region 78 of the material 44 (or single layer region if only a single layer of material is utilized initially). Providing the absorbent assembly 28 can result in successive absorbent article pre-forms 80. In the formation of the resultant absorbent article 10, an absorbent article pre-form 80 can be separated from the remainder of the absorbent article pre-forms 80 at a line of separation 82. The separation of the absorbent article pre-form 80 can occur by any method known to one of ordinary skill in the art. The line of separation 82 bisects each of the quad-laminate regions 76. As a result of the separation of the absorbent article pre-form 80 and the division of the quad-laminate regions 76, a first portion of the quad-laminate regions 76 will become the back side portions, 40 and 42, for a first absorbent article 10 and a second portion of the same quad-laminate regions 76 will become the front side portions, 36 and 38, for a successive absorbent article 10. In various embodiments in which a single layer of material 44 is utilized, the single layer region will become a portion of the chassis 26 in the front waist region 12, back waist region 14, and crotch region 16 and a first portion of the bi-laminate region, as a result of the separation of the absorbent article pre-form 80 and the division of the bi-laminate region, will become the back side portions, 40 and 42, of a first absorbent article 10 and a second portion of the same bi-laminate region will become the front side portions, 36 and 38, of a successive absorbent article 10.

In various embodiments in which the flap 54 can have a rectangular or square shape, the folding of the flap 54 over another portion of the material 44 can ultimately result in front side portions, 36 and 38, and back side portions, 40 and 42, which have a rectangular or square shape. In such embodiments, and in such embodiments in which the side portions, 36, 38, 40 and 42, have a quad-laminate configuration of a liquid permeable material—liquid impermeable material—liquid impermeable material—liquid permeable material, the liquid permeable material can be the material in contact with the wearer's skin, thereby minimizing rubbing of a liquid impermeable material against the wearer's skin. In various embodiments in which the flap 54 is formed by machine direction cuts 50 and/or cross-machine direction cuts 52 which have an arcuate or sinusoidal shape, the resultant flap 54 may not be a rectangular or square shape and may have arcuate or sinusoidal edges. In such embodiments, a portion of a liquid impermeable material may be in contact with the wearer's skin. In such embodiments, the liquid impermeable material can be treated such as, for example, by bonding of a liquid permeable material over the liquid impermeable material or, for example, by treatment with a spray material, such as, for example, a material which can be liquid permeable, to minimize the contact of the liquid permeable material with the wearer's skin when the absorbent article 10 is worn.

To assemble the absorbent article 10, the front waist region 12 can be bonded to the back waist region 14 via the formation of an engagement seam 56 (shown in FIG. 1) between a front side portion, such as front side portion 36, and a back side portion, such as back side portion 40. The engagement seam 56 can be the result of bringing together a first fastening component 66 (such as loops of a hook and loop arrangement) and a second fastening component 68 (such as hooks of a hook and loop arrangement). Any suitable fastening component can be utilized, such as, for example, other types of mechanical fasteners, adhesive fasteners, and/or cohesive fasteners. Each of the front side portions, 36 and 38, and each of the back side portions, 40 and 42, can have a waist end edge 58 disposed towards a longitudinal end of the absorbent article 10. The waist edges, 22 and 24, and the waist end edges, 58 of each of the side portions, 36, 38, 40 and 42, are configured to encircle the waist of the wearer and together at least partially define the central waist opening 60. When worn, the absorbent article 10 has a pair of leg openings which are defined at least in part by the longitudinal side edges, 18 and 20, and the side portions, 36, 38, 40 and 42.

In various embodiments, the absorbent article 10, in accordance with the process of the present disclosure, can have a one-piece chassis 26 which can have a bi-laminate region 78 in the front waist region 12, back waist region 14 and crotch region 16 and can have a quad-laminate region 76 in the front side portions, 36 and 38, and in the back side portions, 40 and 42. In such embodiments, at least a portion of at least two of the side portions, 36, 38, 40 or 42, can be formed by folding a first portion of the chassis 26 material 44 over a second portion of the chassis 26 material 44. In various embodiments, the absorbent article 10, in accordance with the process of the present disclosure, can have a one-piece chassis 26 which can have a single layer region in the front waist region 12, back waist region 14, and crotch region 16 and can have a bi-laminate region in the front side portions, 36 and 38, and in the back side portions, 40 and 42. In such embodiments, at least a portion of at least two of the side portions, 36, 38, 40 or 42, can be formed by folding a first portion of the chassis 26 material 44 over a second portion of the chassis 26 material 44.

Absorbent Assembly:

The absorbent assembly 28 can be bonded to the chassis 26 along at least the crotch region 16 of the absorbent article 10, such as, for example, by adhesive, ultrasonic bonds, thermal bonds, pressure bonds, or the like. Suitable adhesives can be applied continuously or intermittently as beads, a spray, parallel swirls, or the like. Suitable ultrasonic bonds, pressure bonds, and/or thermal bonds can be formed continuously or intermittently along the absorbent assembly 28 to effect the bonding of the absorbent assembly 28 to the chassis 26.

In various embodiments, the absorbent assembly 28 can be permanently bonded to the chassis 26 which is intended to refer to a bonding that is generally not releasably without some damage or substantially reducing functionality of the components that are permanently bonded. In various embodiments, the absorbent assembly 28 can be releasably bonded to the chassis 26 by refastenable fasteners such as adhesive fasteners, cohesive fasteners, mechanical fasteners (e.g., interlocking geometric shaped materials, such as hooks, loops, bulbs, mushrooms, arrowheads, balls on stems, male and female mating components, buckles, snaps) or the like.

In various embodiments, the absorbent assembly 28 can be bonded to the chassis 26 along any one or more of the crotch region 16, the front waist region 12, and/or the back waist region 14. In various embodiments, the absorbent assembly 28 may be bonded to the chassis 26 along any suitable length and/or area of the chassis 26.

In various embodiments, the absorbent assembly 28 can be generally rectangular in shape having a front edge 110, back edge 112, and a pair of opposing longitudinally extending side edges, 114 and 116. While the absorbent assembly 28 can have a rectangular shape, additional shapes are contemplated by this disclosure. In various embodiments, the front edge 110 and the back edge 112 of the absorbent assembly 28 can define respective portions of the front and back waist edges, 22 and 24, respectively, of the absorbent article 10. In various embodiments, the front edge 110 and the back edge 112 of the absorbent assembly 28 can be spaced inward from the front and back waist edges, 22 and 24, respectively, of the absorbent article 10. In such embodiments, the front and back waist edges, 22 and 24, respectively, of the absorbent article 10 will be defined solely by the chassis 26. In various embodiments, the side edges, 114 and 116, of the absorbent assembly 28 can be spaced inward from the side edges, 18 and 20, of the absorbent article 10. In various embodiments, the side edges, 114 and 116, of the absorbent assembly 28 can form portions of the side edges, 18 and 20, of the absorbent article 10. In various embodiments, the front edge 110 and/or the back edge 112 of the absorbent assembly 28 can be folded over (in a direction away from the chassis 26) to create a pocket.

In various embodiments, the absorbent assembly 28 can include a backsheet 120 and a bodyside liner 122 bonded to the backsheet 120 in a superposed relation by suitable means, such as, for example, adhesives, ultrasonic bonds, pressure bonds, thermal bonds or other conventional techniques. An absorbent body 124 can be disposed between the backsheet 120 and the bodyside liner 122. A pair of containment flaps, 126 and 128, can be integrally formed with the absorbent assembly 28 for inhibiting the lateral flow of body exudates.

Figure 5:
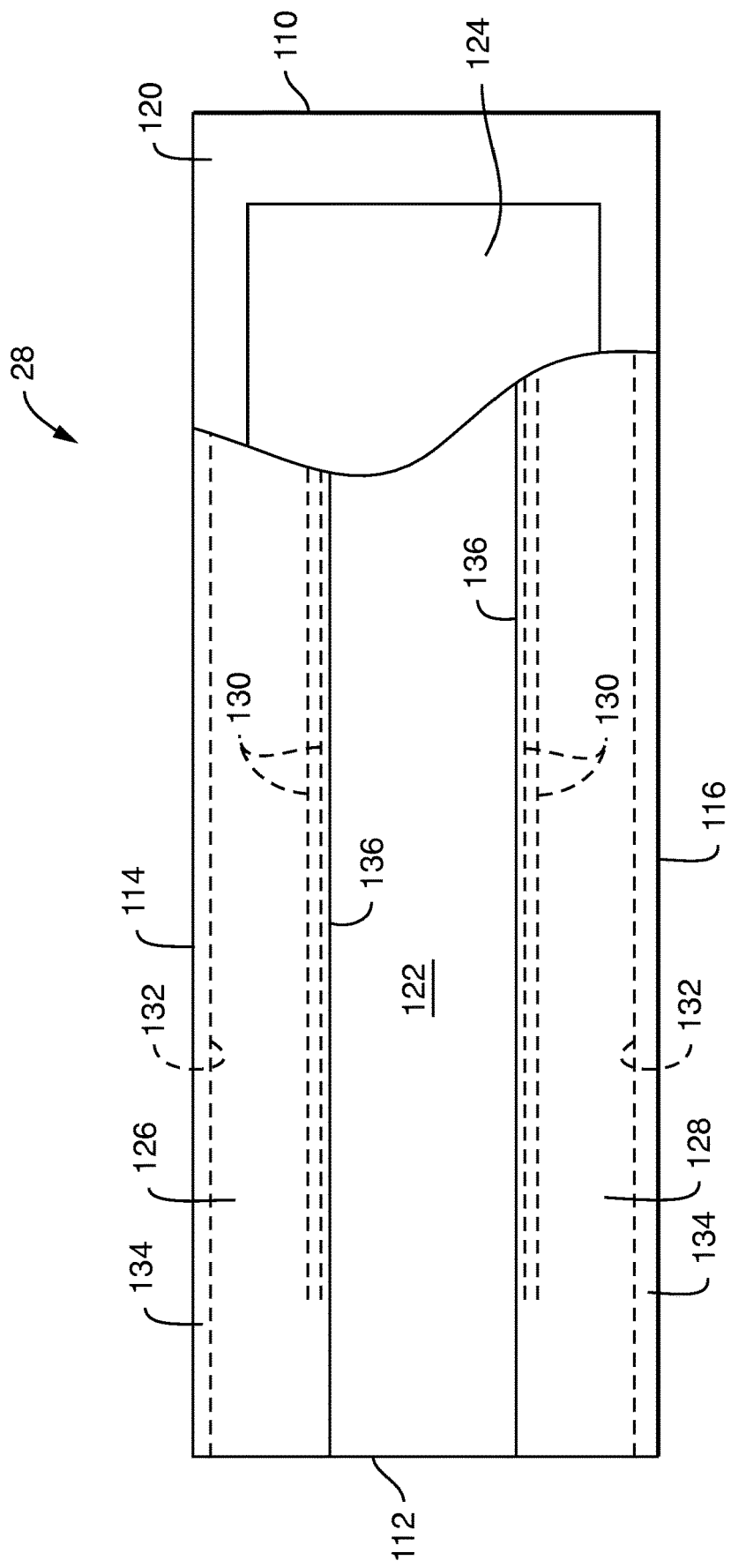
FIG. 5 is a top plan view of an embodiment of an absorbent assembly.

FIG. 5 is a top plan view of an exemplary embodiment of an absorbent assembly 28. As illustrated in FIG. 5, the absorbent assembly 28 can include a backsheet 120, a bodyside liner 122, an absorbent body 124, and containment flaps, 126 and 128.

Backsheet:

In various embodiments, the backsheet 120 can comprise a material which can be substantially liquid impermeable. The backsheet 120 can be a single layer of a liquid impermeable material, or may comprise a multi-layered laminate structure in which at least one of the layers is liquid impermeable. Multiple layers of the backsheet 120 can be bonded together by adhesive, ultrasonic bonds, pressure bonds, thermal bonds, or the like. Suitable adhesives can be applied continuously or intermittently as beads, a spray, parallel swirls, or the like.

The backsheet 120 can be both liquid and vapor impermeable, or, more suitably, it may be liquid impermeable and vapor permeable. The backsheet 120 can be manufactured from a thin plastic film, although other flexible liquid impermeable materials may also be used. The backsheet 120 can prevent body exudates from wetting articles, such as bed sheets and clothing, as well as the wearer and caregiver.

In various embodiments, the liquid impermeable material can permit vapors to escape from the interior of the absorbent article 10 while still preventing liquids from passing through the backsheet 120. A suitable "breathable" material can be composed of a microporous polymer film or a nonwoven fabric that has been coated or otherwise treated to impart a desired level of liquid impermeability.

In various embodiments, the backsheet 120 can comprise a liquid permeable material, or the backsheet 120 can be omitted from the absorbent assembly 28 altogether. In such embodiments, the chassis 26 suitably comprises a liquid impermeable material to provide a liquid barrier to body exudates. In various embodiments in which a backsheet 120 is omitted, the bodyside liner 122 can be bonded to the chassis 26 such that the absorbent body 124 is disposed between the bodyside liner 122 and the inner surface of the chassis 26. In various embodiments, both the absorbent body 124 and the bodyside liner 122 are bonded to the chassis 26.

In various embodiments, the backsheet 120 can be stretchable, and more suitably elastic. In various embodiments, the backsheet 120 is suitably stretchable and more suitably elastic in at least the transverse, or circumferential direction of the absorbent article 10. In various embodiments, the backsheet 120 may be stretchable, and more suitably elastic, in both the transverse and the longitudinal direction.

Absorbent Body:

The absorbent body 124 can be suitably constructed to be generally compressible, conformable, pliable, non-irritating to the wearer's skin and capable of absorbing and retaining liquid body waste, such as urine. The absorbent body 124 can be manufactured in a wide variety of sizes and shapes (for example, rectangular, trapezoidal, T-shape, I-shape, hourglass shape, etc.) and from a wide variety of materials. The size and the absorbent capacity of the absorbent body 124 should be compatible with the size of the intended wearer and the liquid loading imparted by the intended use of the absorbent article 10. Additionally, the size and the absorbent capacity of the absorbent body 124 can be varied to accommodate wearers ranging from infants to adults.

The absorbent body 124 may have a length ranging from about 200, 210, 220, 225, 230, 240, 250, 260, 270, 280, 290, 300, 310, 320, 330, 340, or 350 mm to about 355, 360, 380, 385, 390, 395, 400, 410, 415, 420, 425, 440, 450, 460, 480, 500, 510, 520, 550, 575, 600, 625, 650, 675, 700, 725, 750, 775, 800, 825, 850, 875 or 900 mm. The absorbent body 124 may have a crotch width ranging from about 50, 55, 60, 65, or 70 mm to about 75, 80, 85, 90, 95, 100, 105, 110, 115, 120, 125, 130, 140, 150, 160, 170 or 180 mm. The width of the absorbent body 124 located within the front waist region 12 and/or the back waist region 14 of the absorbent article 10 may range from about 80, 85, 90, or 95 mm to about 100, 105, 110, 115, 120, 125 or 130 mm. As noted herein, the absorbent body 124 can have a length and width that can be less than the length and width of the absorbent article 10.

In an embodiment, the absorbent article 10 can be a diaper pant having the following ranges of lengths and widths of an absorbent body 124 having an hourglass shape: the length of the absorbent body 30 may range from about 200, 210, 220, 225, 240 or 250 mm to about 260, 280, 300, 310, 320, 330, 340, 350, 355, 360, 380, 385, or 390 mm; the width of the absorbent body 124 in the crotch region 16 may range from about 50, 55, or 60 mm to about 65, 70, 75, or 80 mm; the width of the absorbent body 124 in the front waist region 12 and/or the back waist region 14 may range from about 80, 85, 90, or 95 mm to about 100, 105, or 110 mm.

In an embodiment, the absorbent article 10 may be a training pant or youth pant having the following ranges of lengths and widths of an absorbent body 124 having an hourglass shape: the length of the absorbent body 124 may range from about 400, 410, 420, 440 or 450 mm to about 460, 480, 500, 510 or 520 mm; the width of the absorbent body 124 in the crotch region 16 may range from about 50, 55, or 60 mm to about 65, 70, 75, or 80 mm; the width of the absorbent body 124 in the front waist region 12 and/or the back waist region 14 may range from about 80, 85, 90, or 95 mm to about 100, 105, 110, 115, 120, 125, or 130 mm.

In an embodiment, the absorbent article 10 can be an adult incontinence garment having the following ranges of lengths and widths of an absorbent body 124 having a rectangular shape: the length of the absorbent body 124 may range from about 400, 410 or 415 to about 425 or 450 mm; the width of the absorbent body 124 in the crotch region 16 may range from about 90, or 95 mm to about 100, 105, or 110 mm. It should be noted that the absorbent body 124 of an adult incontinence garment may or may not extend into either or both the front waist region 12 or the back waist region 14 of the absorbent article 10.

In an embodiment, the absorbent body 124 can be composed of a web material of hydrophilic fibers, cellulosic fibers (e.g., wood pulp fibers), other natural fibers, synthetic fibers, woven or nonwoven sheets, scrim netting or other stabilizing structures, superabsorbent material, binder materials, surfactants, selected hydrophobic materials, pigments, lotions, odor control agents or the like, as well as combinations thereof. In an embodiment, the absorbent body 124 can be a matrix of cellulosic fluff and superabsorbent hydrogel-forming particles. The absorbent body 124 may be constructed of a single layer of materials, or in the alternative, may be constructed of two layers of materials or more.

In an embodiment in which the absorbent body 124 has two layers, the absorbent body 124 can have a wearer facing layer suitably composed of hydrophilic fibers and a garment facing layer suitably composed at least in part of a high absorbency material commonly known as superabsorbent material. In an embodiment, the wearer facing layer of the absorbent body 124 can be suitably composed of cellulosic fluff, such as wood pulp fluff, and the garment facing layer of the absorbent body 124 can be suitably composed of superabsorbent hydrogel-forming particles, or a mixture of cellulosic fluff and superabsorbent hydrogel-forming particles. As a result, the wearer facing layer can have a lower absorbent capacity per unit weight than the garment facing layer. The wearer facing layer may alternatively be composed of a mixture of hydrophilic fibers and superabsorbent material, as long as the concentration of superabsorbent material present in the wearer facing layer is lower than the concentration of superabsorbent material present in the garment facing layer so that the wearer facing layer can have a lower absorbent capacity per unit weight than the garment facing layer. It is also contemplated that the garment facing layer may be composed solely of superabsorbent material without departing from the scope of this disclosure. It is also contemplated that, in an embodiment, each of the layers, the wearer facing and garment facing layers, can have a superabsorbent material such that the absorbent capacities of the two superabsorbent materials can be different and can provide the absorbent body 124 with a lower absorbent capacity in the wearer facing layer than in the garment facing layer.

Various types of wettable, hydrophilic fibers can be used in the absorbent body 124. Examples of suitable fibers include cellulosic fibers, synthetic fibers composed of cellulose or cellulose derivatives, such as rayon fibers; inorganic fibers composed of an inherently wettable material, such as glass fibers; synthetic fibers made from inherently wettable thermoplastic polymers, such as particular polyester or polyamide fibers or composed of nonwettable thermoplastic polymers, such as polyolefin fibers which have been hydrophilized by suitable means. The fibers may be hydrophilized, for example, by treatment with a surfactant, treatment with silica, treatment with a material which has a suitable hydrophilic moiety and is not readily removed from the fiber, or by sheathing the nonwettable, hydrophobic fiber with a hydrophilic polymer during or after formation of the fiber. For example, one suitable type of fiber is a wood pulp that is a bleached, highly absorbent sulfate wood pulp containing primarily soft wood fibers. However, the wood pulp can be exchanged with other hydrophilic fiber materials, such as synthetic, polymeric, or meltblown fibers or with a combination of meltblown and natural fibers.

In an embodiment, the cellulosic fluff can include a blend of wood pulp fluff. An example of wood pulp fluff can be "Bowater CoosAbsorb S Fluff Pulp" or equivalent available from Bowater, Greenville, S.C., U.S.A. which is a bleached, highly absorbent sulfate wood pulp containing primarily southern soft wood fibers. The absorbent web can be formed with a dry-forming technique, an air forming technique, a wet-forming technique, a foam-forming technique, or the like, as well as combinations thereof. Methods and apparatus for carrying out such techniques are well known in the art.

Suitable superabsorbent materials can be selected from natural, synthetic, and modified natural polymers and materials. The superabsorbent materials can be inorganic materials, such as silica gels, or organic compounds, such as cross-linked polymers. Cross-linking may be covalent, ionic, Van der Waals, or hydrogen bonding. Typically, a superabsorbent material can be capable of absorbing at least about ten times its weight in liquid. In an embodiment, the superabsorbent material can absorb more than 24 times its weight in liquid. Examples of superabsorbent materials include polyacrylamides, polyvinyl alcohol, ethylene maleic anhydride copolymers, polyvinyl ethers, hydroxypropyl cellulose, carboxymal methyl cellulose, polyvinylmorpholinone, polymers and copolymers of vinyl sulfonic acid, polyacrylates, polyacrylamides, polyvinyl pyrrolidone, and the like. Additional polymers suitable for superabsorbent material include hydrolyzed, acrylonitrile grafted starch, acrylic acid grafted starch, polyacrylates and isobutylene maleic anhydride copolymers and mixtures thereof. The superabsorbent material may be in the form of discrete particles. The discrete particles can be of any desired shape, for example, spiral or semi-spiral, cubic, rod-like, polyhedral, etc. Shapes having a largest greatest dimension/smallest dimension ratio, such as needles, flakes, and fibers are also contemplated for use herein. Conglomerates of particles of superabsorbent materials may also be used in the absorbent body 124. In an embodiment, the absorbent body 124 can have at least about 50% by weight of a superabsorbent material. In an embodiment, the absorbent body 124 can have at least about 50, 55, 60, 65, 70, 75, 80, 85, 90, 95, 99 or 100% by weight of a superabsorbent material. Examples of superabsorbent material include, but are not limited to, FAVOR SXM-9300 or equivalent available from Evonik Industries, Greensboro, N.C., U.S.A. and HYSORB 8760 or equivalent available from BASF Corporation, Charlotte, N.C., U.S.A.

The absorbent body 124 can be superposed over the inner layer of the backsheet 120 and can be bonded to the inner layer of the backsheet 120, such as by being bonded thereto with adhesive. However, it is to be understood that the absorbent body 124 may be in contact with, and unbounded with, the backsheet 120 and remain within the scope of this disclosure.

Bodyside Liner:

The bodyside liner 122 of the absorbent assembly 28 can overlay the absorbent body 124 and the backsheet 120 and can isolate the wearer's skin from liquid waste retained by the absorbent body 124. The bodyside liner 122 may also overlay an acquisition layer and may be bonded to the acquisition layer. In an embodiment, the bodyside liner 122 can extend beyond the absorbent body 124 and/or the acquisition layer to overlay a portion of the inner layer of the backsheet 120 and can be bonded thereto by any method deemed suitable, such as, for example, by being bonded thereto by adhesive, to substantially enclose the absorbent body 124 between the backsheet 120 and the bodyside liner 122. The bodyside liner 122 may be slightly narrower than the backsheet 120, but it is to be understood that the bodyside liner 122 and the backsheet 120 may be of the same dimensions. It is also contemplated that the bodyside liner 122 may not extend beyond the absorbent body 124 and may not be secured to the backsheet 120. The bodyside liner 122 can be suitably compliant, soft feeling, and non-irritating to the wearer's skin and can be less hydrophilic than the absorbent body 124 to provide a relatively dry surface to the wearer and permit liquid body waste to readily penetrate through its thickness.

The bodyside liner 122 can be manufactured from a wide selection of web materials, such as synthetic fibers (for example, polyester or polypropylene fibers), natural fibers (for example, wood or cotton fibers), a combination of natural and synthetic fibers, porous foams, reticulated foams, apertured plastic films, or the like. Various woven and non-woven fabrics can be used for the bodyside liner 122. For example, the bodyside liner 122 can be composed of a meltblown or spunbond web of polyolefin fibers. Alternatively, the bodyside liner 122 can be a bonded-carded web composed of natural and/or synthetic fibers. The bodyside liner 122 can be composed of a substantially hydrophobic material, and the hydrophobic material can, optionally, be treated with a surfactant or otherwise processed to impart a desired level of wettability and hydrophilicity. The surfactant can be applied by any conventional means, such as spraying, printing, brush coating or the like. The surfactant can be applied to the entire bodyside liner 122 or it can be selectively applied to particular sections of the bodyside liner 122.

In an embodiment, a bodyside liner 122 can be constructed of a non-woven bicomponent web. The non-woven bicomponent web can be a spunbonded bicomponent web, or a bonded-carded bicomponent web. An example of a bicomponent staple fiber includes a polyethylene/polypropylene bicomponent fiber. In this particular bicomponent fiber, the polypropylene forms the core and the polyethylene forms the sheath of the fiber. Fibers having other orientations, such as multi-lobe, side-by-side, end-to-end may be used without departing from the scope of this disclosure. In an embodiment, a bodyside liner 122 can be a 12 gsm spunbond-meltblown-spunbond substrate having 10% meltblown content applied between the two spunbond layers.

In an embodiment, the bodyside liner 122 can have a basis weight less than about 30 gsm. In an embodiment, the bodyside liner 122 can have a basis weight less than about 30, 28, 26, 24, 22, 20, 18, 16, 14 or 12 gsm. In an embodiment, the bodyside liner 122 can have a basis weight from about 6, 8, 10, 12, 14, 16, or 18 gsm to about 20, 22, 24, 26, 28 or 30 gsm.

Although the backsheet 120 and bodyside liner 122 can include elastomeric materials, it is contemplated that the backsheet 120, the bodyside liner 122 and the absorbent body 124 can be composed of materials which are generally non-elastomeric. In an embodiment, the bodyside liner 122 can be stretchable, and more suitably elastic. In an embodiment, the bodyside liner 122 can be suitably stretchable and more suitably elastic in at least the lateral or circumferential direction of the absorbent article 10. In other aspects, the bodyside liner 122 can be stretchable, and more suitably elastic, in both the lateral and the longitudinal directions.

Fluid Transfer Layer:

In an embodiment, the absorbent assembly 28 can have a fluid transfer layer (not shown). The fluid transfer layer can have a wearer facing surface and a garment facing surface. In an embodiment, the garment facing surface of the fluid transfer layer can be bonded to the wearer facing surface of the absorbent body 124. Bonding of the garment facing surface of the fluid transfer layer to the wearer facing surface of the absorbent body 124 can occur through the use of adhesive. In an embodiment, the fluid transfer layer can completely encompass the absorbent body 124 and can be sealed to itself. In an embodiment, the fluid transfer layer may be folded over on itself and then sealed using, for example, heat and/or pressure. In an embodiment, the fluid transfer layer may be composed of separate sheets of material which can be utilized to partially or fully encompass the absorbent body 124 and which can be sealed together using a sealing means such as an ultrasonic bonder or other thermochemical bonding means or the use of an adhesive.

In an embodiment, the fluid transfer layer can be bonded with only the wearer facing surface of the absorbent body 124. In an embodiment, the fluid transfer layer can be bonded with the wearer facing surface and at least one of the edges of the absorbent body 124. In an embodiment, the fluid transfer layer can be bonded with the wearer facing surface, at least one of the edges and the garment facing surface of the absorbent body 124. In an embodiment, the absorbent body 124 may be partially or completely encompassed by the fluid transfer layer.

The fluid transfer layer can be pliable, less hydrophilic than the absorbent body 124, and sufficiently porous to be liquid permeable to thereby permit liquid to penetrate through its thickness to reach the absorbent body 124. In an embodiment, the fluid transfer layer can have sufficient structural integrity to withstand wetting thereof and of the absorbent body 124. In an embodiment, the fluid transfer layer can be constructed from a single layer of material or it may be a laminate constructed from two or more layers of material.

A common fluid transfer layer is an absorbent cellulosic material such as creped wadding or a high-strength tissue. A disadvantage of this common type of fluid transfer layer is a deficiency of wet strength to maintain structural integrity of the absorbent body 124. In an embodiment, the fluid transfer layer can be a laminate of a meltblown nonwoven material having fine fibers, laminated to at least one, spunbond nonwoven material layer having coarse fibers. In such an embodiment, the fluid transfer layer can be a spunbond-meltblown ("SM") material. In an embodiment, the fluid transfer layer can be a spunbond-meltblown-spunbond ("SMS") material. A non-limiting example of such a fluid transfer layer can be a 10 gsm spunbond-meltblown-spunbond material. In an embodiment, the fluid transfer layer can be composed of at least one material which has been fluid entangled into a nonwoven substrate. In an embodiment, the fluid transfer layer can be composed of at least two materials which have been fluid entangled into a nonwoven substrate. In an embodiment, the fluid transfer layer can have at least three materials which have been fluid entangled into a nonwoven substrate. A non-limiting example of a fluid transfer layer can be a 33 gsm fluid entangled substrate. In such an example, the fluid transfer layer can be a 33 gsm fluid entangled substrate composed of a 12 gsm spunbond material, a 10 gsm wood pulp material having a length from about 0.6 cm to about 5.5 cm, and an 11 gsm polyester staple fiber material. To manufacture the fluid transfer layer just described, the 12 gsm spunbond material can provide a base layer while the 10 gsm wood pulp material and the 11 gsm polyester staple fiber material can be homogeneously mixed together and deposited onto the spunbond material and then fluid entangled with the spunbond material. In an embodiment, a wet strength agent can be included in the fluid transfer layer. A non-limiting example of a wet strength agent can be Kymene 6500 (557LK) or equivalent available from Ashland Inc. of Ashland, Ky., U.S.A.

In an embodiment, the fluid transfer layer can be bonded with an absorbent body 124 which is made at least partially of particulate material such as superabsorbent material. In an embodiment in which the fluid transfer layer at least partially or completely encompasses the absorbent body 124, the fluid transfer layer should not unduly expand or stretch as this might cause particulate material to escape from the absorbent body 124. In an embodiment, the fluid transfer layer, while in a dry state, should have respective elongation values at peak load in the machine and cross directions of 30 percent or less and 40 percent or less. In an embodiment, the fluid transfer layer may have a longitudinal length the same as the longitudinal length of the absorbent body 124.

In an embodiment, the fluid transfer layer can have a basis weight less than about 40 gsm. In an embodiment, the fluid transfer layer can have a basis weight less than about 40, 39, 38, 37, 36, 35, 34, 33, 32, 31, 30, 25, 20, 15, or 10 gsm. In an embodiment, the fluid transfer layer can have a basis weight from about 10, 15, 20, 25, or 30 gsm to about 31, 32, 33, 34, 35, 36, 37, 38, 39, or 40 gsm Acquisition Layer:

In an embodiment, the absorbent assembly 28 can have an acquisition layer (not shown). The acquisition layer can help decelerate and diffuse surges or gushes of liquid body waste penetrating the bodyside liner 122. In an embodiment, the acquisition layer can be positioned between the bodyside liner 122 and the absorbent body 124 to take in and distribute urine for absorption by the absorbent body 124. In an embodiment, the acquisition layer can be positioned between the bodyside liner 122 and a fluid transfer layer.

The acquisition layer may have any longitudinal length dimension as deemed suitable. The acquisition layer may have a longitudinal length from about 120, 130, 140, 150, 160, 170, 180, 190, 200, 210, 220, 225, 230, 240, or 250 mm to about 260, 270, 280, 290, 300, 310, 320, 340, 350, 360, 380, 400, 410, 415, 420, 425, 440, 450, 460, 480, 500, 510 or 520 mm. In an embodiment, the acquisition layer can have any length such that the acquisition layer can be coterminous with the front and back edges, 110 and 112, of the absorbent assembly 28. In an embodiment, the longitudinal length of the acquisition layer can be the same as the longitudinal length of the absorbent body 124. In such an embodiment the midpoint of the longitudinal length of the acquisition layer can substantially align with the midpoint of the longitudinal length of the absorbent body 124.

The acquisition layer may have any width as desired. The acquisition layer may have a width dimension from about 15, 20, 25, 30, 35, 40, 45, 50, 55, 60, or 70 mm to about 80, 90, 100, 110, 115, 120, 130, 140, 150, 160, 170, or 180 mm. The width of the acquisition layer may vary dependent upon the size and shape of the absorbent article 10 within which the acquisition layer will be placed. The acquisition layer can have a width smaller than, the same as, or larger than the width of the absorbent body 124. Within the crotch region 16 of the absorbent article 10, the acquisition layer can have a width smaller than, the same as, or larger than the width of the absorbent body 124.

In an embodiment, the acquisition layer can be a through-air bonded-carded web such as a 35 gsm through-air bonded-carded web composite composed of a homogeneous mixture of about 35% sheath/core bicomponent polyethylene/polypropylene fibers having a fiber diameter of 6 denier, about 35% sheath/core bicomponent polyethylene/polypropylene fibers having a fiber diameter of 2 denier, and about 30% polyester fibers having a fiber diameter of 6 denier. An example of such a composite is a composite composed of about 35% Huvis 180-N (PE/PP6d), about 35% Huvis N-215 (PE/PP 2d), and about 30% Huvis SD-10 PET 6d, or equivalent composite, available from SamBo Company, Ltd, Korea.

The acquisition layer may have additional parameters including basis weight and thickness. In an embodiment, the basis weight of the acquisition layer can be at least about 20 gsm. In an embodiment, the basis weight of the acquisition layer can be from about 20, 30, 40, 50 or 60 gsm to about 65, 70, 75, 80, 85, 90, 100 gsm. In an embodiment, the basis weight of the acquisition layer can be less than about 100, 90, 85, 80, 75, 70, 65, 60 or 50 gsm. In an embodiment, the acquisition layer can have a thickness, measured at 0.05 psi, of less than about 1.5 mm. In an embodiment, the acquisition layer can have a thickness, measured at 0.05 psi, of less than about 1.5, 1.25, or 1.0 mm.

Containment Flaps:

The absorbent assembly 28 can have an opposing pair of longitudinally extending containment flaps, 126 and 128. Each of the containment flaps, 126 and 128, can be formed as extensions of the bodyside liner 122, portions of which can extend beyond the lateral width of the absorbent assembly 28 can be folded laterally inwards about a longitudinal fold line, such that the extended portion of the bodyside liner 122 can come into a face-to-face relations with a laterally inward portion of the bodyside liner 122 along a central region of the absorbent assembly 28. Each containment flap, 126 and 128, can have flap elastic members 130.

The folded region of the containment flaps, 126 and 128, can be suitably bonded to the bodyside liner 122 by an adhesive seam 132 extending longitudinally along the absorbent assembly 28, thereby forming a fixed edge 134. Suitable adhesives can be applied continuously or intermittently to the bodyside liner 122 as beads, a spray, parallel swirls, or the like. The adhesive seams 132 can extend any suitable length along the crotch region 16 of the absorbent article 10.

The containment flaps, 126 and 128, can each have a free edge 136. The free edge 136 is disposed opposite the fixed edge 134, and is configured to assume an upright configuration in at least the crotch region 16 of the absorbent article 10. The flap elastic members 130 are positioned proximate the free edge 134 such that when a tensile force is applied to the flap elastic members 130, the free edges 134 of the containment flaps, 126 and 128, assume an upright configuration to form a seal against the wearer's body during use.

The flap elastic members 130 may be forms of sheets, strands or ribbons of natural rubber, synthetic rubber, or thermoplastic elastomeric polymers. The elastic materials can be stretched and adhered to a substrate and then elasticized or shrunk, for example with the application of heat, such that elastic retractive forces are imparted to the substrate.

The flap elastic members 130 can extend any suitable length along the containment flaps, 126 and 128. In various embodiments, the flap elastic members 130 can extend less than the full length of the containment flaps, 126 and 128. In various embodiments, the flap elastic members 130 extend along the containment flaps, 126 and 128, only within the crotch region 16 of the absorbent article 10. In various embodiments, the flap elastic members 130 are generally coextensive with the absorbent body 124.

The flap elastic members 130 can include active portions (i.e., portions of the flap elastic member 130 that are elastic) and inactive portions (i.e., portions of the flap elastic member 130 that are non-elastic). Portions of the flap elastic members 130 can be rendered inactive by, for example, chopping or otherwise "deadening" the flap elastic members 130 along a desired inactive portion. The flap elastic members 130 can include any suitable number of active and inactive portions having any suitable dimension and configuration.

Waist Elastic Members:

In various embodiments, the absorbent article 10 can have waist elastic members, such as front waist elastic member 46 and back waist elastic member 48 (shown in FIG. 1) which can be formed of any suitable elastic material. In such an embodiment, suitable elastic materials can include, but are not limited to, sheets, strands or ribbons of natural rubber, synthetic rubber, or thermoplastic elastomeric polymers. The elastic materials can be stretched and bonded to a substrate, bonded to a gathered substrate, or bonded to a substrate and then elasticized or shrunk, for example, with the application of heat, such that elastic retractive forces are imparted to the substrate. The waist elastic members, 46 and 48, can be bonded to the inner surface of the chassis 26 (i.e., the surface of the chassis 26 that faces the wearer when worn) or the outer surface of the chassis (i.e., the surface of the chasses that faces away from the wearer). The waist elastic members, 46 and 48, can be bonded to the chassis 26 in the central portion 34 of the chassis 26. In various embodiments, the waist elastic members, 46 and 48, can be bonded to the chassis 26 in the central portion 34 of the chassis 26 and in the front side portions, 36 and 38, and the back side portions, 40 and 42. It is to be understood, however, that the waist elastic members, 46 and 48, may be omitted from the absorbent article 10 without departing from the scope of this disclosure.

When introducing elements of the present disclosure or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements. Many modifications and variations of the present disclosure can be made without departing from the spirit and scope thereof. Therefore, the exemplary embodiments described above should not be used to limit the scope of the invention.

What is claimed is:

1. An absorbent article comprising:
   a. a one-piece chassis comprising a chassis material comprising one or more layers and defining a front waist region, a back waist region, and a crotch region interconnecting the front waist region and the back waist region;
   b. an opposing pair of front side portions integral with the chassis in the front waist region;
   c. an opposing pair of back side portions integral with the chassis in the back waist region; and
   d. at least two of the front side portions or the back side portions are formed of a first portion of the chassis material folded onto a second portion of the chassis material forming a laterally extending fold in each of the layers of the chassis material.

2. The absorbent article of claim 1 wherein the chassis material is a single layer of material.

3. The absorbent article of claim 1 wherein the chassis material is a laminate of two layers of material.

4. The absorbent article of claim 3 wherein a first layer of material is a liquid permeable material and a second layer of material is a liquid impermeable material.

5. The absorbent article of claim 4 wherein each of the side portions comprises a wearer facing surface and a garment facing surface and a portion of the liquid permeable material is located on at least a portion of the wearer facing surface of each of the side portions.

6. The absorbent article of claim 1 further comprising an absorbent assembly bonded to the chassis.

7. The absorbent article of claim 1 wherein the chassis material is at least stretchable in a lateral direction.

8. The absorbent article of claim 1, wherein each of the opposing pair of front side portions and each of the opposing pair of back side portions comprise a longitudinal dimension and a lateral dimension, and wherein the laterally extending fold extends through the entire lateral dimension of each of the at least two of the front side portions or the back side portions.

9. The absorbent article of claim 1, wherein each of the opposing pair of front side portions and each of the opposing pair of back side portions comprise a laterally extending inner longitudinal edge disposed proximate the crotch region and a laterally extending outer longitudinal edge disposed distal the crotch region, and wherein the laterally extending fold extends along the entire inner longitudinal edges of each of the at least two of the front side portions or the back side portions.

10. The absorbent article of claim 1, wherein each of the opposing pair of front side portions and each of the opposing pair of back side portions comprise a laterally extending inner longitudinal edge disposed proximate the crotch region and a laterally extending outer longitudinal edge disposed distal the crotch region, and wherein the laterally extending fold extends along the entire outer longitudinal edges of each of the at least two of the front side portions or the back side portions.

11. The absorbent article of claim 1, wherein only one pair of the front side portions or the back side portions comprise the laterally extending fold.

12. The absorbent article of claim 1, wherein the front side portions comprise front waist end edges and the rear side portions comprise rear waist end edges, and wherein the laterally extending fold extends substantially parallel to the front waist end edge or the rear waist end edge of the at least two of the front side portions or the back side portions.

13. An absorbent article comprising:
   a. a one-piece chassis comprising a chassis material comprising one or more layers and defining a front waist region, a back waist region, and a crotch region interconnecting the front waist region and the back waist region;
   b. an opposing pair of front side portions integral with the chassis in the front waist region;
   c. an opposing pair of back side portions integral with the chassis in the back waist region;
   d. at least two of the front side portions or the back side portions are formed of a first portion of the chassis material folded onto a second portion of the chassis material forming a laterally extending fold in each layer of the chassis material; and
   e. an absorbent assembly bonded to the chassis material, wherein the laterally extending fold extends substantially perpendicular to the absorbent assembly.

14. The absorbent article of claim 13 wherein the chassis material is a single layer of material.

15. The absorbent article of claim 13 wherein the chassis material is a laminate of two layers of material.

16. The absorbent article of claim 15 wherein a first layer of material is a liquid permeable material and a second layer of material is a liquid impermeable material.

17. The absorbent article of claim 16 wherein each of the side portions comprises a wearer facing surface and a garment facing surface and a portion of the liquid permeable material is located on at least a portion of the wearer facing surface of each of the side portions.

18. The absorbent article of claim 13 wherein the chassis material is at least stretchable in a lateral direction.

* * * * *